(12) United States Patent
Gevgilili et al.

(10) Patent No.: US 11,026,870 B2
(45) Date of Patent: Jun. 8, 2021

(54) SYSTEMS, COMPOSITIONS, AND METHODS FOR CLEANSING AND DETOXIFYING KERATIN FIBERS

(71) Applicant: L'OREAL, Paris (FR)

(72) Inventors: Halil Gevgilili, Weehawken, NJ (US); Jun Liang, Staten Island, NY (US); Heather Lee, Wayne, NJ (US); Semra Senturk-Ozer, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/399,559

(22) Filed: Apr. 30, 2019

(65) Prior Publication Data

US 2019/0328636 A1   Oct. 31, 2019

Related U.S. Application Data

(60) Provisional application No. 62/664,802, filed on Apr. 30, 2018.

(51) Int. Cl.
| | |
|---|---|
| *C11D 3/10* | (2006.01) |
| *A61K 8/26* | (2006.01) |
| *A61K 8/19* | (2006.01) |
| *A61K 8/42* | (2006.01) |
| *A61K 8/46* | (2006.01) |
| *A61Q 5/02* | (2006.01) |

(52) U.S. Cl.
CPC ............... *A61K 8/26* (2013.01); *A61K 8/19* (2013.01); *A61K 8/42* (2013.01); *A61K 8/463* (2013.01); *A61Q 5/02* (2013.01); *A61K 2800/222* (2013.01); *A61K 2800/596* (2013.01); *A61K 2800/882* (2013.01)

(58) Field of Classification Search
CPC .. C11D 3/10; C11D 3/128; C11D 9/12; C11D 3/0094; C11D 3/0052; C11D 3/1253
See application file for complete search history.

(56) References Cited

U.S. PATENT DOCUMENTS

| | | |
|---|---|---|
| 6,566,408 B1 | 5/2003 | Cotrell et al. |
| 7,709,436 B2 | 5/2010 | Theiler et al. |
| 9,198,838 B2 * | 12/2015 | Glenn, Jr. ............... A61K 8/463 |
| 2005/0113279 A1 * | 5/2005 | Desmarescaux ...... C11D 3/3942 510/447 |
| 2012/0095120 A1 | 4/2012 | Braun et al. |
| 2013/0281342 A1 * | 10/2013 | Ambrosen ............ A61K 8/0237 510/135 |
| 2014/0288191 A1 | 9/2014 | Kim et al. |
| 2015/0056296 A1 * | 2/2015 | Hiki ......................... A61K 8/19 424/613 |
| 2016/0067155 A1 * | 3/2016 | Shimada .............. A61K 8/0212 424/44 |
| 2017/0151157 A1 | 6/2017 | Gevgilili et al. |
| 2017/0281522 A1 | 10/2017 | Gevgilili et al. |
| 2018/0055751 A1 | 3/2018 | Gevgilili et al. |

FOREIGN PATENT DOCUMENTS

| | | |
|---|---|---|
| EP | 0399157 A2 | 11/1990 |
| EP | 0692244 A1 | 1/1996 |
| JP | S61-293908 A | 12/1986 |
| JP | 2017-109964 A | 6/2017 |
| WO | 2012/072765 A1 | 6/2012 |
| WO | 2016/016439 A1 | 2/2016 |

OTHER PUBLICATIONS

Non-Final Office Action for copending U.S. Appl. No. 16/399,598, dated Jun. 10, 2020.
Cosmetic Ingredient Review, Safety Assessment of Polyglyceryl Fatty Acid Esters as Used in Cosmetics, Mar. 7, 2016 (Year: 2016).
International Search Report and Written Opinion for counterpart Application No. PCT/US2019/029981, dated Jul. 25, 2019.
International Search Report and Written Opinion for counterpart Application No. PCT/US2019/029994, dated Aug. 22, 2019.
Final Office Action for copending U.S. Appl. No. 16/399,598, dated Jan. 21, 2021.
International Preliminary Report on Patentability for counterpart Application No. PCT/US2019/029981, dated Nov. 12, 2020.
International Preliminary Report on Patentability for counterpart Application No. PCT/US2019/029994, dated Nov. 12, 2020.

* cited by examiner

*Primary Examiner* — Charles I Boyer
(74) *Attorney, Agent, or Firm* — The Marbury Law Group, PLLC

(57) ABSTRACT

The disclosure relates to systems and compositions for cleansing and detoxifying keratin fibers, in particular human keratin fibers such as the hair, as well as processes for cleansing and detoxifying keratin fibers using the systems and compositions according to the disclosure.

10 Claims, No Drawings

SYSTEMS, COMPOSITIONS, AND METHODS FOR CLEANSING AND DETOXIFYING KERATIN FIBERS

TECHNICAL FIELD

The present disclosure relates to systems and compositions for cleansing and detoxifying keratin fibers, in particular human keratin fibers such as the hair, as well as methods for cleansing and detoxifying keratin fibers using the systems and compositions according to the disclosure.

BACKGROUND

In order to improve the appearance of their hair, consumers routinely subject their hair to mechanical and/or chemical treatments such as combing and brushing the hair, application of heat to the hair with a hair dryer or curling/straightening iron, chemical processes such as hair coloring, bleaching, straightening, permanent waving, and the like, cleansing processes such as shampooing, and styling the hair using products such as gels, mousses, pomades, and sprays. However, such treatments can lead to dry and damaged hair. Furthermore, exposure to environmental agents such as UV radiation, salt, or chlorine can likewise have a drying and damaging effect on the hair. Finally, compositions and treatments that consumers use on a regular basis, such as daily, weekly, etc., may lead to a build-up of products on the hair that can leave hair dull and lacking volume and smoothness. Thus, consumers desire compositions to treat dry and damaged hair, remove product buildup, and balance pH.

Carbon dioxide-generating agents, such as sodium bicarbonate, are known for household and personal-care use. However, such agents are difficult to formulate in aqueous solutions for personal-care use because of their intrinsic equilibrium with carbon dioxide which results in formation of carbon dioxide. When excessive carbon dioxide gas forms, it creates gas pockets that make the formulations too difficult and unpleasant to use.

Therefore, it is an object of the disclosure to provide systems and compositions using carbon dioxide-generating agents for cleansing and detoxifying keratin fibers, which have acceptable properties of stability and sensoriality. The systems and compositions may be particularly advantageous for users who have dry hair, product buildup, or as mid-cycle treatment for rejuvenating hair.

SUMMARY

The present disclosure relates to systems, compositions, and methods for cleansing and detoxifying keratin fibers. The systems, compositions, and methods according to the disclosure use carbon dioxide-generating agents and clays to provide a cleansing and detoxifying mask for the hair and scalp.

According to one embodiment, the disclosure relates to systems comprising: (a) an additive composition comprising (i) at least one carbon dioxide-generating compound, and (ii) at least one clay; and (b) a shampoo composition; wherein the additive composition and the shampoo composition are combined to form a cleansing composition at or near the time of use. According to various embodiments of systems, the at least one carbon dioxide-generating compound is chosen from carbonate or bicarbonate salts of alkaline metals or alkaline earth metals, and the at least one clay is chosen from silicate-based clays. In yet further embodiments of systems, the at least one carbon dioxide-generating compound comprises sodium bicarbonate, and the at least one clay comprises magnesium aluminum silicate.

According to further embodiments, the disclosure relates to methods for cleansing keratin fibers, the methods comprising (1) mixing an additive composition comprising at least one carbon dioxide-generating compound and at least one clay with a shampoo composition to form a cleansing composition; (2) applying the cleansing composition to the keratin fibers; and (3) optionally rinsing the cleansing composition from the keratin fibers. According to various embodiments of methods, the at least one carbon dioxide-generating compound is chosen from carbonate or bicarbonate salts of alkaline metals or alkaline earth metals, and the at least one clay is chosen from silicate-based clays. In yet further embodiments of methods, the at least one carbon dioxide-generating compound comprises sodium bicarbonate, and the at least one clay comprises magnesium aluminum silicate.

According to yet further embodiments, the disclosure relates to systems comprising: (a) an additive composition comprising (i) sodium bicarbonate, and (ii) magnesium aluminum silicate; and (b) a shampoo composition comprising at least one cleansing surfactant; wherein the additive composition and the shampoo composition are combined to form a cleansing composition at or near the time of use; and methods of cleansing keratin fibers with the systems disclosed.

According to yet further embodiments, the disclosure relates to kits, the kits comprising (1) a first compartment comprising an additive composition comprising at least one carbon dioxide-generating compound and at least one clay; and (2) a second compartment comprising a shampoo composition; wherein the additive composition and the shampoo composition are in mutually separate compartments.

Still further embodiments relate to multi-chamber containers, the multi-chamber containers comprising (1) a first chamber comprising an additive composition comprising at least one carbon dioxide-generating compound and at least one clay; and (2) a second chamber comprising a shampoo composition; wherein the additive composition and the shampoo composition are in mutually separate chambers.

Yet further embodiments relate to containers comprising from about 10-40% sodium bicarbonate, by weight of the additive composition, and from about 60-90% magnesium aluminum silicate, by weight of the additive composition.

In further embodiments, the disclosure relates to systems comprising (a) an additive composition comprising at least one clay; and (b) a shampoo composition comprising at least one carbon dioxide-generating compound; wherein the additive composition and the shampoo composition are combined to form a cleansing composition at or near the time of use. According to various embodiments of systems, the at least one carbon dioxide-generating compound is chosen from carbonate or bicarbonate salts of alkaline metals or alkaline earth metals, and the at least one clay is chosen from silicate-based clays. In yet further embodiments of systems, the at least one carbon dioxide-generating compound comprises sodium bicarbonate, and the at least one clay comprises magnesium aluminum silicate.

Kits and containers are also disclosed. For example, kits comprising (1) a first compartment comprising an additive composition comprising at least one clay; and (2) a second compartment comprising a shampoo composition comprising at least one carbon dioxide-generating compound; wherein the additive composition and the shampoo composition are in mutually separate compartments, are disclosed. Likewise, multi-chamber containers comprising (1) a first chamber comprising an additive composition comprising at least one clay; and (2) a second chamber comprising a shampoo composition comprising at least one carbon dioxide-generating compound; wherein the additive composition and the shampoo composition are in mutually separate chambers, are disclosed. According to various embodiments of kits and containers, the at least one carbon dioxide-generating compound is chosen from carbonate or bicarbonate salts of alkaline metals or alkaline earth metals, and the at least one clay is chosen from silicate-based clays. In yet further embodiments of kits and containers, the at least one carbon dioxide-generating compound comprises sodium bicarbonate, and the at least one clay comprises magnesium aluminum silicate Methods of cleansing keratin fibers, the methods comprising (1) mixing an additive composition comprising at least one clay with a shampoo composition comprising at least one carbon dioxide-generating compound to form a cleansing composition; (2) applying the cleansing composition to the keratin fibers; and (3) optionally rinsing the cleansing composition from the keratin fibers, are also disclosed. According to various embodiments of methods, the at least one carbon dioxide-generating compound is chosen from carbonate or bicarbonate salts of alkaline metals or alkaline earth metals, and the at least one clay is chosen from silicate-based clays. In yet further embodiments of methods, the at least one carbon dioxide-generating compound comprises sodium bicarbonate, and the at least one clay comprises magnesium aluminum silicate.

DESCRIPTION

The present disclosure relates to a system comprising two compositions for preparing a cleansing and detoxifying hair and scalp mask. The first composition is an additive composition, and the second composition is a shampoo composition. The system forms a cleansing and detoxifying mask for keratin fibers, such as the hair and scalp, when the first and second compositions are mixed at or near the time of use. The disclosure also relates to processes of cleansing and detoxifying the hair and scalp using the systems and compositions according to the disclosure. The disclosure also relates to kits comprising the system and compositions according to the disclosure, as well as multi-chamber containers comprising a shampoo composition in one chamber and an additive composition in a separate chamber. Finally, the disclosure relates to an additive composition to be used in conjunction with a shampoo composition.

Systems

The systems according to the disclosure comprise two compositions that, when combined, form a cleansing and detoxifying hair and scalp mask composition. The first composition is an additive composition, and the second composition is a shampoo composition. The additive composition may be used in conjunction with the shampoo composition. According to various embodiments, the combination of the additive composition and shampoo composition provides a cleansing and detoxifying mask composition comprising carbon dioxide-generating agents and clays.

Additive Compositions

According to various embodiments, the additive compositions may comprise clays. In further embodiments, the additive compositions may comprise carbon dioxide-generating agents and clays.

The additive composition comprises at least one clay. The clay may, in certain embodiments be chosen from silicate-based clays. By way of non-limiting example, Aluminum Silicate, Calcium Silicate, Magnesium Aluminum Silicate, Magnesium Silicate, Magnesium Trisilicate, Sodium Magnesium Silicate, Zirconium Silicate, Attapulgite, Bentonite, Fuller's Earth, Hectorite, Kaolin, Lithium Magnesium Silicate, Lithium Magnesium Sodium Silicate, Montmorillonite, Pyrophyllite, Zeolite, or mixtures thereof may be used.

The at least one clay may be present in the additive composition in individual or total combined amounts of at least 10% by weight of the additive composition, such as at least 20%, at least 30%, at least 40%, at least 50%, at least 55%, at least 60%, at least 65%, at least 70%, at least 75%, at least 80%, at least 85%, at least 90%, or at least 95%, by weight of the additive composition. It is to be understood that the clay can be present in the additive composition in a range having any of the aforementioned numbers as either a low or high end of the range.

In various embodiments, the at least one clay may be present in the additive composition in individual or total combined amounts ranging from 10% to 99% by weight of the additive composition. For example, the clay may be present in an amount ranging from 15% to 99%, such as 20% to 95%, 30% to 95%, 40% to 90%, 45% to 90%, 50% to 85%, 55% to 85%, 60% to 85%, 65% to 85%, 70% to 85%, 70% to 80%, or about 75%, by weight of the additive composition. In further embodiments, the at least one clay may be present in the additive composition in individual or total combined amounts ranging from 10% to 40%, such as 10% to 35%, 15% to 30%, 15% to 25%, or 20% to 25%.

If present in the additive composition, the carbon dioxide-generating compound may be chosen from, for example, at least one carbonate or bicarbonate salt of at least one alkaline metal or alkaline earth metal. Non-limiting examples of carbonates and bicarbonates that can be used include sodium carbonate, potassium carbonate, magnesium carbonate, calcium carbonate, sodium bicarbonate, potassium bicarbonate, magnesium bicarbonate, calcium bicarbonate, as well as mixtures thereof. More than one carbon dioxide-generating compound may be chosen in certain embodiments.

The carbon dioxide-generating compound may be present in the additive composition in individual or combined amounts of at least 1% by weight of the additive composition, such as at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, or at least 50%, by weight of the additive composition. It is to be understood that the carbon dioxide-generating compound can be present in the additive composition in a range having any of the aforementioned numbers as either a low or high end of the range.

In various embodiments, the carbon dioxide-generating compound may be present in the additive composition in individual or combined amounts ranging from 1% to 80% by weight of the additive composition. For example, the carbon dioxide-generating compound may be present in an amount ranging from 2% to 80%, such as 5% to 80%, 5% to 75%, 10% to 70%, 10% to 60%, 10% to 50%, 15% to 40%, 15% to 35%, 15% to 30%, 20% to 30%, 20% to 25%, or about 25%, by weight of the additive composition.

In various embodiments, the additive composition may be in dry form such as in the form of a mixture of solids, e.g. a dried powder or granule mixture, may be a semi-solid form such as a paste or thickened gel, or may be a liquid or semi-liquid form such as a solution, an emulsion, etc. In one exemplary embodiment, the additive composition is in dry form, e.g. a powder or granules, which can be mixed with a solvent such as water at or near the time of use.

In at least certain embodiments, the additive composition may be in the form of a two-part composition, where the carbon dioxide-generating compound and the at least one clay are separate, and are mixed with the shampoo composition individually. In such embodiments, the above-mentioned amounts and ratios are contemplated for the carbon dioxide-generating compounds and clays.

The additive composition may optionally comprise additional components. As non-limiting examples, the additive composition may comprise pigments, additional thickeners, film formers, antioxidants, essential oils, botanical extracts, fragrances, preserving agents, emollients, moisturizers, and vitamins.

By way of example, pigments that can be used in the additive composition include pearlescent pigments mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

If present, the additional, optional components may be present, individually or in total, in amounts up to 5%, such as up to 4%, up to 3%, up to 2%, up to 1%, up to 0.5%, up to 0.05%, or up to 0.01%, by weight of the additive composition. It is to be understood that the additional, optional components may individually or in total be present in the additive composition in a range having any of the aforementioned numbers as either a low or high end of the range. For example, the additive composition may comprise additional, optional components individually or in total in an amount ranging from 0.01% to 5%, such as 0.05% to 2%, or 0.1% to 1%, by weight of the additive composition.

According to various embodiments where the additive composition comprises a carbon dioxide-generating compound, the additive composition may contain the carbon dioxide-generating compound and clay in a ratio of carbon dioxide-generating compound:clay ranging from 4:1 to 1:10. For example, the ratio of carbon dioxide-generating compound:clay may range from 3:1 to 1:9, such as 2:1 to 1:8, 1:1 to 1:7, 1:1 to 1:6, 1:1 to 1:5, 1:2 to 1:4, or about 1:3, including all ranges and subranges therebetween. In one exemplary and non-limiting embodiment, the additive composition comprises sodium bicarbonate and magnesium aluminum silicate in a ratio of about 1:3.

In at least certain exemplary and non-limiting embodiments, the additive composition is a dry composition, e.g. a solid, mixed powder or granule composition, or is a semi-solid paste composition, comprising sodium bicarbonate in an amount ranging from 10% to 40%, such as 20% to 30%, and magnesium aluminum silicate in an amount ranging from 60% to 90%, such as 70% to 80%. In yet further exemplary and non-limting embodiments, the additive composition comprises magnesium aluminum silicate in an amount ranging from 15% to 30%, such as 20% to 25%.

Shampoo Compositions

The shampoo composition may be any conventional shampoo composition comprising cleansing surfactants, and optionally further comprising conditioning agents and/or at least one carbon dioxide-generating compound. The shampoo composition may, for example, be a conventional liquid shampoo composition.

The shampoo composition may also be those that employ anionic (cleansing) surfactants chosen from sulfate-based compounds, non-sulfate-based compounds, and mixtures thereof. Thus, shampoo compositions may be sulfate-based shampoos or sulfate-free shampoos.

Useful and non-limiting cleansing surfactants may be chosen from anionic, amphoteric, and nonionic cleansing surfactants. For example, useful anionic cleansing surfactants may be chosen from salts of each of alkyl sulfates, alkyl ether sulfates, acyl isethionates, acyl glycinates, acyl taurates, acyl amino acids, acyl sarcosinates, sulfosuccinates, sulfonates, isethionates, wherein the alkyl and acyl groups of these compounds comprise from 6 to 40 carbon atoms. Exemplary anionic cleansing surfactants include Sodium Laureth Sulfate, Sodium Lauryl Sulfate, Ammonium Lauryl Sulfate, Ammonium Laureth Sulfate, Sodium Cocoyl Isethionate, Sodium Lauroyl Methyl Isethionate, Sodium Cocoyl Methyl Isethionate, Tea-Cocoyl Glutamate, Sodium Lauroyl Glutamate, Disodium Cocoyl Glutamate, Sodium Cocoyl Glutamate, Sodium Cocoyl Alaninate, Sodium Cocyl Glycinate, Disodium Laureth Sulfosuccinate, Sodium Lauryl Sulfoacetate (and) Disodium Laureth Sulfosuccinate, Lauryl Phosphate, Lauryl Phospate and Potassium Phosphate, Sodium Methyl Cocoyl Taurate, Sodium Lauroyl Sarcosinate, Sodium Cocoyl Sarcosinate, Sodium Lauryl Glucose Carboxylate, and mixtures thereof.

Further useful and non-limiting cleansing surfactants may be chosen from amphoteric surfactants, such as betaines, sultaines, amphoacetates, amphoproprionates, and mixtures thereof. Exemplary amphoteric surfactants include Coco Betaine, Cocamidopropyl Betaine, Cocamidopropyl betaine and glyceryl laurate capryl/capramidopropyl betaine, Lauryl betaine, Cocamidopropyl hydroxysultaine, sodium cocoamphodiacetate, sodium cocoamphoacetate, sodium cocoamphopropionate, and mixtures thereof.

Further useful and non-limiting cleansing surfactants may be chosen from nonionic surfactants, such as alkyl polyglucosides, alkanolamides, glycol ethers, amine oxides, and mixtures thereof. Exemplary nonionic cleansing surfactants include lauryl glucoside, decyl glucoside, coco glucoside, Cocamide MIPA, PEG-8 glyceryl laurate, polysorbate-40, polyglyceryl-5 laurate, lauryl amine oxide, and mixtures thereof.

If present, useful and non-limiting conditioning agents include cationic surfactants and polymers. For example, polyquaterium-10, cetrimonium chloride, behentrimonium chloride, behentrimonium methosulfate, steartrimonium chloride, stearalkonium chloride and dicetyldimonium chloride, cetrimonium chloride, quaternium-22, behenylamidopropyl-2, 3-di-hydroxypropyldimethylammonium chloride, palmitylamidopropyltrimethylammonium chloride, and chloride and methyl sulfate of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethyl-ammonium, distearyldimethylammonium chloride, oleocetyldimethylhydroxyethylammonium chloride, stearamidopropyldimethyl (myristyl acetate) ammonium chloride, di(C1-C2 alkyl) (C12-C22 alkyl)hydroxy(C1-C2alkyl)ammonium salt, or alkyltrimethylammonium salt in which the alkyl radical comprises 12 to 24 carbon atoms, propanetallowdiammonium dichloride, behentrimonium methosulfate, quaternium-83, quaternium-87, and mixtures thereof may be chosen. In various embodiments, guar gums and derivatives, such as hydroxypropyl guar hydroxypropyltrimonium chloride, may be chosen as conditioning agents.

If present in the shampoo composition, carbon dioxide-generating compounds may be chosen from, for example, at least one carbonate or bicarbonate salt of at least one alkaline metal or alkaline earth metal. Non-limiting examples of carbonates and bicarbonates that can be used include sodium carbonate, potassium carbonate, magnesium carbonate, calcium carbonate, sodium bicarbonate, potassium bicarbonate, magnesium bicarbonate, calcium bicarbonate, as well as mixtures thereof. More than one carbon dioxide-generating compound may be chosen in certain embodiments.

If present in the shampoo composition, the carbon dioxide-generating compound may be present in individual or combined amounts of at least 1% by weight of the shampoo composition, such as at least 2%, at least 3%, at least 4%, at least 5%, at least 6%, at least 7%, at least 8%, at least 9%, at least 10%, at least 11%, at least 12%, at least 13%, at least 14%, or at least 15%, by weight of the shampoo composition. It is to be understood that the carbon dioxide-generating compound can be present in the shampoo composition in a range having any of the aforementioned numbers as either a low or high end of the range.

In various embodiments, the carbon dioxide-generating compound may be present in the shampoo composition in individual or combined amounts ranging from 1% to 15%, such as 2% to 12%, 3% to 10%, 4% to 8%, or 5% to 7%, by weight of the shampoo composition. In further exemplary embodiments, the carbon dioxide-generating compound may be present in the shampoo composition in individual or combined amounts ranging from 2% to 8%, 3% to 7%, 4% to 6%, or about 5%.

According to various embodiments, for example when the shampoo composition comprises at least one carbon dioxide-generating compound, the pH of the shampoo composition may range from 3 to 10, such as 4 to 10, 5 to 10, 6 to 10, 7 to 10, 8 to 10, 8 to 9, or 8.5 to 9. In other embodiments, for example when the shampoo composition does not comprise at least one carbon dioxide-generating compound, the pH of the shampoo composition may range from 3 to 10, such as 4 to 9, 4 to 8, 4 to 7, 4.5 to 6, 5 to 5.5, or about 5.3.

The shampoo composition may optionally comprise other additional components traditionally used in shampoo compositions. For example, the shampoo composition may optionally additionally comprise natural and synthetic oils, humectants, shine agents, fillers, colorants, pigments, chelating agents, sequestering agents, fragrances, preservatives, stabilizers, thickeners/viscosity adjusters, pH adjusters, and mixtures thereof.

By way of example only, liquid shampoo compositions such as those disclosed in U.S. Publication Nos. 2018/0055751, 2017/0281522, and 2017/0151157, and in WO2012/072765, may be used.

Any of the additive and/or shampoo compositions of the present invention may comprise a solvent chosen from water, solvents other than water such as cosmetically acceptable organic solvents, and mixtures thereof. Suitable examples of cosmetically acceptable solvents are glycols, polyols, short chain or lower carbon alcohols.

Cleansing and Detoxifying Mask and Methods of Cleansing and Detoxifying Hair

The system comprised of a first shampoo composition and a second additive composition are mixed to form a cleansing and detoxifying mask composition. According to various embodiments, the shampoo composition and additive composition can be mixed at or near the time of use to form a mask composition, which can be applied to hair and scalp to cleanse and detoxify the hair and scalp. In various embodiments, the hair and scalp may be subsequently optionally rinsed.

As used herein, mixing "at or near the time of use" is intended to convey that the mixing typically occurs substantially immediately before use, for example up to 1 minute before use, such as up to 2 minutes, up to 5 minutes, up to 10 minutes, up to 15 minutes, up to 20 minutes, up to 30 minutes, up to 60 minutes, up to 2 hours, up to 6 hours, up to 12 hours, or up to 24 hours before use. Although not required, the mixing at or near the time of use may be performed or effected by the user, who may be an individual cleansing their own hair or the hair of another person (e.g. at a salon). Any form of mixing of the additive composition and shampoo composition is contemplated.

As used herein, language indicating that the additive composition is "used in conjunction with" a shampoo composition is intended to mean that the additive composition and shampoo composition are applied to the hair at substantially the same time, preferably without an intermediate step of rinsing. In one exemplary embodiment, the additive composition and liquid shampoo composition may be dispensed from separate containers and mixed in the user's hand or on the user's head. In another exemplary embodiment, the additive composition and liquid shampoo composition may be dispensed substantially simultaneously from a multi-chamber container to the user's hand or head. Thus, "mixed" as used herein should not be limited to mixing prior to application to the keratin fibers. It is to be understood, therefore, that the disclosure is not intended to be limiting as to the manner or order of dispensing or mixing of the additive and/or shampoo compositions.

The cleansing and detoxifying mask may be prepared by mixing the additive composition and shampoo composition in any ratio useful for preparing a mask-like texture of the cleansing composition. For example, the additive composition:shampoo composition may be mixed in a ratio of 1:10 to 1:0.1, such as 1:6 to 1:05, 1:5 to 1:05, 1:4 to 1:1; 1:2 to 1:1, about 1:4, or about 1:1. For example, the additive composition:shampoo composition may be mixed in a ratio of 1:10, 1:9, 1:8, 1:7, 1:6, 1:5, 1:4, 1:3, 1:2, 1:1, 1:05, or 1:01, it being understood that the ratio can be any range having any of the aforementioned numbers as either a low or high end of the range.

The mask may be left on the hair and/or scalp for any period of time, such as up to 1 minutes, up to 2 minutes, up to 3 minutes, up to 4 minutes, up to 5 minutes, up to 6 minutes, up to 7 minutes, up to 8 minutes, up to 9 minutes, up to 10 minutes, up to 15 minutes, up to 20 minutes, up to 30 minutes, up to 1 hour, up to 2 hours, up to 6 hours, up to 12 hours, or more, as desired. The mask may optionally be rinsed from the hair after a desired period of time.

It should be understood that the term "mask" as used herein is to indicate that the cleansing and detoxifying mask composition is creamy with a traditional mask-like consistency and feel, and does not foam, at least not substantially, upon mixing of the additive and shampoo compositions. However, unless otherwise clearly indicated, the term "mask" should not be interpreted to be limiting regarding any particular viscosity or consistency of the cleansing composition prepared by mixing the additive composition and shampoo composition as described herein.

Kits and Containers

The disclosure also relates to kits and containers comprising an additive composition, and optionally a shampoo composition, according to the disclosure.

According to various embodiments, kits for cleansing and detoxifying the hair and scalp may be multi-compartment kits, where the compartments are mutually separate. For example, the kits may comprise at least two compartments, with a first compartment containing an additive composition and a second compartment containing a shampoo composition, according to the disclosure.

The compartments of kits according to the disclosure can be in any configuration, without limitation. For example, they can be a bottle, a tube, a sachet, an ampoule, or any other container configured to contain the additive composition or shampoo composition mutually separately in the kit.

One exemplary embodiment of a kit for cleansing and detoxifying the hair comprises: a first compartment containing an additive composition comprising:
  i. at least one carbon dioxide-generating compound; and
  ii. at least one clay; and
a second compartment containing a shampoo composition.

A further exemplary embodiment of a kit for cleansing and detoxifying the hair comprises a first compartment containing an additive composition comprising at least one clay, and a second compartment comprising a shampoo composition comprising at least one carbon dioxide-generating compound.

A further exemplary embodiment of a kit for cleansing and detoxifying the hair comprises: a first compartment containing an additive composition comprising:
  i. sodium bicarbonate; and
  ii. magnesium aluminum silicate; and
a second compartment containing a shampoo composition.

Yet a further exemplary embodiment of a kit for cleansing and detoxifying the hair comprises a first compartment containing an additive composition comprising magnesium aluminum silicate, and a second compartment comprising a shampoo composition comprising sodium bicarbonate.

Various embodiments of containers for containing both the additive composition and shampoo composition according to the disclosure can be used. For example, a multi-chamber container may be chosen, where a first chamber comprises an additive composition according to the disclosure and a second chamber contains a shampoo composition.

By way of example only, a container having at least two mutually separate storage chambers, the first of which contains an additive composition and the second of which contains a shampoo composition, each of whose contents can be removed simultaneously by means of two separate outlets. In various embodiments, the ratio of the discharged amount of additive composition to shampoo composition is predetermined to be delivered simultaneously to the user and then mixed in the user's hand or on the user's head. As a further example, a container having at least two mutually separate storage chambers, the first of which contains an additive composition and the second of which contains a shampoo composition, each of whose contents can be removed simultaneously through a common outlet, where mixing optionally occurs in a common chamber leading to the common outlet. In various embodiments, the ratio of the discharged amount of additive composition to shampoo composition is predetermined to be delivered, for example in an already-mixed form, to the user. Such multi-chamber containers may be, for example, pump containers or squeeze containers.

One exemplary embodiment of a multi-chamber container for cleansing the hair comprises: a first chamber containing an additive composition comprising:
  i. at least one carbon dioxide-generating compound; and
  ii. at least one clay; and
a second chamber containing a shampoo composition. A further exemplary embodiment of a multi-chamber container for cleansing the hair comprises a first chamber containing an additive composition comprising at least one clay, and a second chamber containing a liquid shampoo composition comprising at least one carbon dioxide-generating compound.

A further exemplary embodiment of a multi-chamber container for cleansing the hair comprises: a first chamber containing an additive composition comprising:
  i. sodium bicarbonate; and
  ii. magnesium aluminum silicate; and
a second chamber containing a liquid shampoo composition.

Yet a further exemplary embodiment of a multi-chamber container for cleansing the hair comprises a first chamber containing an additive composition comprising magnesium aluminum silicate, and a second chamber containing a liquid shampoo composition comprising sodium bicarbonate.

In yet further exemplary embodiments, the container may be a bottle, a tube, a sachet, an ampoule, or any other container configured to contain the additive composition separate from any container comprising a shampoo composition. In such embodiments, the additive composition can be used with any shampoo composition of the user's choice.

According to various exemplary embodiments, advantages associated with the cleansing and detoxifying mask compositions include excellent hair and scalp cleansing, detoxifying, and purifying properties, and excellent added fullness, body, and volume to the hair after treatment. It should be noted, however, that embodiments that do not impart one or more of the advantages are still within the scope of the disclosure.

It is to be understood that all definitions herein are provided for the present disclosure only.

It is to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. The term "about" is used herein to indicate a difference of up to +/−10% from the stated number, such as +/−9%, +/−8%, +/−7%, +/−6%, +/−5%, +/−4%, +/−3%, +/−2%, or +/−1%.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples that follow serve to illustrate embodiments of the present disclosure without, however, being limiting in nature.

It will be apparent to those skilled in the art that various modifications and variations can be made in the additive composition, shampoo composition, cleansing mask composition, and methods, kits, and containers of the invention without departing from the spirit or scope of the invention. Thus, it is intended that the present invention cover the modifications and variations of this invention provided that they come within the scope of the appended claims and their equivalents.

EXAMPLES

The ingredient amounts in the compositions/formulations described below are expressed in % by weight, based on the total weight of the composition, unless otherwise indicated.

Example 1

Cleansing Mask 1

Example 1A

Shampoo Composition

A shampoo composition was prepared as shown in Table 1A.

TABLE 1A

| Ingredient | Example 1A - Shampoo |
| --- | --- |
| Cocamide MIPA | 3 |
| Sodium Laureth Sulfate | 11 |
| Sodium Lauryl Sulfate | 4 |
| Preservatives | 0.7 |
| Hydroxypropyl guar hydroxypropyltrimonium chloride | 0.4 |
| Additional Ingredients | 0 to <3.0 wt. % |
| Water | q.s. 100 |

Example 1B

Additive Composition

An additive composition was prepared by combining sodium bicarbonate with magnesium aluminum silicate to form a dry powder mix, as shown in Table 1B.

TABLE 1B

| Ingredient | Example 1B - Additive |
| --- | --- |
| Sodium Bicarbonate | 25 |
| Magnesium Aluminum Silicate | 75 |

Example 1C

Cleansing Mask 1 Composition

A mask for cleansing hair and scalp was prepared by mixing the shampoo composition of Example 1A with the additive composition of Example 1B in about 4:1 ratio to create a mixture with a paste-like texture and foaming capacity. The resultant mask composition is shown in Table 1C.

TABLE 1C

| Ingredient | Example 1C - Mask 1 |
| --- | --- |
| Sodium Bicarbonate | 5 |
| Magnesium Aluminum Silicate | 15 |
| Cocamide MIPA | 2.4 |
| Sodium Laureth Sulfate | 8.8 |
| Sodium Lauryl Sulfate | 3.2 |
| Preservatives | 0.6 |
| Hydroxypropyl Guar Hydroxypropyltrimonium Chloride | 0.3 |
| Additional Ingredients | 0 to <3.0 wt. % |
| Water | q.s. 100 |

Example 2

Cleansing Mask 2

Example 2A

Shampoo Composition

A shampoo composition was prepared as shown in Table 2A.

TABLE 2A

| Ingredient | Example 2A - Shampoo |
| --- | --- |
| Cocamide MIPA | 3 |
| Sodium Laureth Sulfate | 11 |
| Sodium Lauryl Sulfate | 4 |
| Sodium Bicarbonate | 5 |
| Hydroxypropyl guar hydroxypropyltrimonium chloride | 0.4 |
| Additional Ingredients | 0 to <3.0 wt. % |
| Water | q.s. 100 |

Example 2B

Additive Composition

An additive composition was prepared by combining the components in Table 2B to form a paste.

TABLE 2B

| Ingredient | Example 2B - Additive |
|---|---|
| Magnesium Aluminum Silicate | 11 |
| Kaolin | 11 |
| Cetearyl alcohol (and) Ceteareth-20 | 2 |
| Caprylic/capric triglyceride | 1.8 |
| Polymers (corn starch, xantham gum) | 1.3 |
| Additional Ingredients | 0 to <10.0 wt. % |
| Water | q.s. 100 |

Example 2C

Cleansing Mask 2 Composition

A second cleansing mask composition was prepared by mixing the shampoo composition of Example 2A with the additive composition of Example 2B in a 1:1 ratio. The resultant mask composition is shown in Table 2C.

TABLE 2C

| Ingredient | Example 2C - Mask 2 |
|---|---|
| Magnesium Aluminum Silicate | 5.5 |
| Kaolin | 5.5 |
| Sodium Bicarbonate | 2.5 |
| Cocamide MIPA | 1.5 |
| Sodium Laureth Sulfate | 5.5 |
| Sodium Lauryl Sulfate | 2 |
| Polymers (corn starch, xantham gum) | 0.65 |
| Caprylic/capric triglyceride | 0.9 |
| Cetearyl alcohol (and) Ceteareth-20 | 1 |
| Hydroxypropyl guar hydroxypropyltrimonium chloride | 0.2 |
| Additional Ingredients | 0 to <6.0 wt. % |
| Water | q.s. 100 |

Example 3

Method for Cleansing and Detoxifying Hair and Scalp

The mask composition of Example 1C (inventive composition) was used on 10 subjects, and its performance and effects were evaluated and compared to a commercial shampoo without the additive composition (comparative composition). The comparative shampoo composition contained sulfate-based anionic surfactants including sodium lauryl sulfate, sodium laurest sulfate, and sodium xylenesulfonate.

Users of the inventive composition reported that it had a paste-like, creamy texture and was easy to prepare by mixing.

The inventive composition was applied to the hair on half of the head of each test subject, and the comparative composition was applied to the other half of the head of each test subject. Both products were lathered into the hair and scalp and then rinsed out with water. The hair was subsequently blow dried.

Hair treated with the inventive composition felt refreshed and looked and felt thicker and fuller (i.e., it had more body and volume), compared to the hair treated with the comparative composition. The hair treated with the inventive composition also felt smooth and silky without the need for additional products and appeared movable, healthy, and breathable.

The invention claimed is:

1. A method for cleansing keratin fibers comprising:
   (1) mixing a first composition comprising:
      a) at least one carbon dioxide-generating compound selected from the group consisting of carbonate or bicarbonate salts of alkaline metals or alkaline earth metals, or mixtures thereof; and
      b) from about 20% to about 85% by weight of the first composition of at least one clay selected from the group consisting of Aluminum Silicate, Calcium Silicate, Magnesium Aluminum Silicate, Magnesium Silicate, Magnesium Trisilicate, Sodium Magnesium Silicate, Zirconium Silicate, Attapulgite, Bentonite, Fuller's Earth, Hectorite, Kaolin, Lithium Magnesium Silicate, Lithium Magnesium Sodium Silicate, Montmorillonite, Pyrophyllite, Zeolite, or mixtures thereof;
   with a second composition comprising a liquid shampoo to form a cleansing composition, wherein the first composition and the second composition are combined to form a cleansing composition at or near the time of use;
   (2) applying the cleansing composition to the keratin fibers; and
   (3) optionally rinsing the cleansing composition from the keratin fibers.

2. The method of claim 1, wherein the carbonate or bicarbonate salts of alkaline metals or alkaline earth metals are selected from the group consisting of sodium carbonate, potassium carbonate, magnesium carbonate, calcium carbonate, sodium bicarbonate, potassium bicarbonate, magnesium bicarbonate, calcium bicarbonate, or mixtures thereof.

3. The method of claim 1, wherein the first composition comprises from about 10 to about 40% by weight of the at least one carbon dioxide-generating compound, relative to the total weight of the first composition.

4. The method of claim 1, wherein the first composition comprises from about 60 to about 85% by weight of the at least one clay relative to the total weight of the first composition.

5. The method of claim 1, wherein the second composition comprises at least one surfactant selected from the group consisting of anionic surfactants, non-ionic surfactants, amphoteric surfactants, or mixtures thereof.

6. The method of claim 1,
   wherein the first composition comprises
      at least one carbon dioxide-generating compound selected from the group consisting of sodium carbonate, potassium carbonate, magnesium carbonate, calcium carbonate, sodium bicarbonate, potassium bicarbonate, magnesium bicarbonate, calcium bicarbonate, or mixtures thereof; and
   wherein the second composition comprises:
      i) at least one cleansing surfactant selected from the group consisting of anionic surfactants, non-ionic surfactants, amphoteric surfactants, or mixtures thereof; and
      ii) optionally, at least one conditioning agent.

7. The method of claim 1, wherein the first composition comprises:
   a) from about 10 to about 40% sodium bicarbonate relative to the total weight of the first composition; and b) from about 60 to about 85% magnesium aluminum silicate and/or kaolin relative to the total weight of the first composition;

wherein the second composition comprises at least one conditioning agent; and wherein the weight ratio of the first composition to the second composition ranges from about 1:7 to about 1:1.

8. The method of claim 1 wherein the first composition comprises:
  a) sodium bicarbonate; and
  b) from about 20% to about 85% by weight of Magnesium Aluminum Silicate and/or kaolin relative to the total weight of the frist composition,
  wherein the second composition at least one cleansing surfactant to form a cleansing composition.

9. The method of claim 8, wherein the first composition comprises:
  a) from about 10 to about 40% sodium bicarbonate relative to the total weight of the first composition;
  b) from about 60 to about 85% magnesium aluminum silicate and/or kaolin relative to the total weight of the first composition;
  wherein the second composition further comprises at least one conditioning agent; and wherein the weight ratio of the first composition to the second composition ranges from about 1:7 to about 1:1.

10. The method of claim 1 wherein the first composition comprises from about 40% to about 85% by weight of the at least one clay relative to the total weight of the first composition.

* * * * *